(12) United States Patent
Sato et al.

(10) Patent No.: US 7,875,722 B2
(45) Date of Patent: Jan. 25, 2011

(54) METHOD FOR PRODUCING QUINOLONE CARBOXYLIC ACID DERIVATIVE

(75) Inventors: Koji Sato, Edogawa-ku (JP); Kenji Sakuratani, Edogawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 12/569,938

(22) Filed: Sep. 30, 2009

(65) Prior Publication Data

US 2010/0063279 A1 Mar. 11, 2010

Related U.S. Application Data

(63) Continuation of application No. PCT/JP2008/000817, filed on Mar. 31, 2008.

(30) Foreign Application Priority Data

Mar. 30, 2007 (JP) .............................. 2007-090650

(51) Int. Cl.
*C07D 215/56* (2006.01)
*C07D 295/155* (2006.01)
*C07D 291/04* (2006.01)
*C07D 265/28* (2006.01)

(52) U.S. Cl. ...................................... 546/123; 546/156
(58) Field of Classification Search ................. 546/123, 546/156
See application file for complete search history.

(56) References Cited

U.S. PATENT DOCUMENTS

| 5,043,450 | A | 8/1991 | Masuzawa et al. |
| 5,869,661 | A | 2/1999 | Ochi et al. |
| 2007/0213339 | A1 | 9/2007 | Khire et al. |

FOREIGN PATENT DOCUMENTS

| EP | 0 342 675 B1 | 11/1989 |
| EP | 0 641 782 | 3/1995 |
| JP | 62-252772 | 11/1987 |
| JP | 63-316757 | 12/1988 |
| JP | 3-95177 | 4/1991 |
| JP | 5-294938 A | 11/1993 |
| JP | 5294938 (A) | 11/1993 |
| JP | 07-309864 | 11/1995 |
| WO | WO 2005/047260 A1 | 5/2005 |
| WO | WO 2005/097752 A1 | 10/2005 |

OTHER PUBLICATIONS

Majid M. Heravi, et al., "Regioselective Synthesis of Quinolone Antibacterials via Borate Complex of Quinolone Carboxylic Acid", Journal of Chemical Research, Sep. 2005, pp. 578-579.
Liu Mingliang, et al., "Graphical Synthetic Routes of Balofloxacin", Chinese Journal of New Drugs, 2004, vol. 13, No. 12, pp. 1130-1133 (with full English translation).
Liu Mingliang, et al., "Synthesis of Moxifloxacin", Chinese Journal of Pharmaceuticals, 2004, 35, (3), pp. 129-131(with full English translation).
Liu Mingliang, et al., "Synthesis of Balofloxacin", Chinese Journal of Pharmaceuticals, 2004, 35,(7), pp. 385-387 (with English translation).

*Primary Examiner*—Kahsay T Habte
(74) *Attorney, Agent, or Firm*—Oblon, Spivak, McClelland, Maier & Neustadt, L.L.P.

(57) ABSTRACT

The present invention relates to a method for producing a quinolone compound having high antibacterial activity and high safety, at high yield and in a simple manner.

A quinolonecarboxylic acid derivative (1) of interest is produced through a one-pot manner by reacting a compound (2) with a salt of a cyclic amine (3) and with a boron derivative in a solvent in the presence of a base.

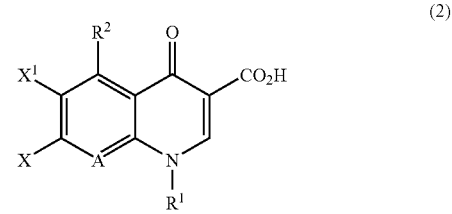

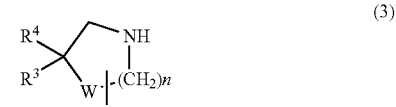

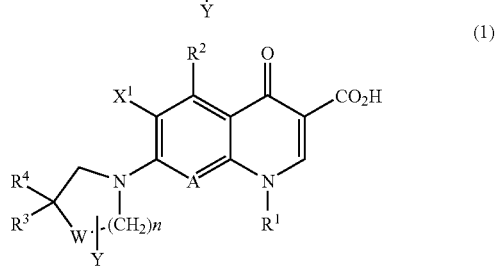

14 Claims, No Drawings

METHOD FOR PRODUCING QUINOLONE CARBOXYLIC ACID DERIVATIVE

CROSS-REFERENCE TO RELATED APPLICATIONS

This application is a continuation of PCT/JP08/000817 filed Mar. 31, 2008 and claims the benefit of JP 07/090650 filed Mar. 30, 2007.

TECHNICAL FIELD

The present invention relates to a method for producing a quinolone compound having high antibacterial activity and high safety, at high yield and in a simple manner.

BACKGROUND ART

Generally, a quinolone compound has a cyclic amine substituent including a second amino moiety at the 7-position (or an equivalent position thereof) of the quinolone skeleton. Such quinolone compounds are generally synthesized by reacting a cyclic amine compound with a 7-halogenated quinolonecarboxylic acid compound. In order to enhance yield and reaction site specificity, the carboxylic acid moiety of a quinolonecarboxylic acid compound is transformed into a borofluoric acid ester moiety or a boric acid ester moiety, followed by reaction with a cyclic amine compound (see Patent Documents 1 to 3 and Non-Patent Documents 1 to 4).

Furthermore, from an industrial viewpoint, there have been developed methods for producing quinolonecarboxylic acid derivatives at high efficiency; e.g., a production method in which an alkyl borate is employed as an additive (Patent Document 4), and a one-pot method (Patent Document 5).

Patent Document 1: JP-A-1987-252772
Patent Document 2: JP-A-1988-316757
Patent Document 3: JP-A-1991-95177
Patent Document 4: JP-A-1993-294938
Patent Document 5: WO 2005/047260
Non-Patent Document 1: Majid M. Heravi et al., Journal of Chemical Research, 2005, 579.
Non-Patent Document 2: Liu Ming-Liang et al., Chinese Journal of New Drugs, 2004, 13, 12, 1130.
Non-Patent Document 3: Liu Ming-Liang et al., Chinese Journal of Pharmaceuticals, 2004, 35, 3, 129.
Non-Patent Document 4: Liu Ming-Liang et al., Chinese Journal of Pharmaceuticals, 2004, 35, 7, 385.

DISCLOSURE OF THE INVENTION

Problems to be Solved by the Invention

When the method disclosed in Patent Document 3 is employed, a free-form amine compound is reacted to give quinolonecarboxylic acid derivatives at a high yield (72 to 81%). However, free-form cyclic amine compounds have less chemical stability and poor handleability, which are problematic. Then, when a salt-form cyclic amine compound, which is excellent in stability and handleability, is employed in a reaction, the quinolonecarboxylic acid derivative yield (49%) do not reach the yield which is obtained by use of a free-form amine compound. Thus, use of such an amine compound salt is still problematic in terms of industrial production.

In the method disclosed in Patent Document 4, no quinolonecarboxylic acid derivative can be produced even when a cyclic amine salt compound having a high stability and high handleability is used. In addition, the method disclosed in Patent Document 4 includes a step of transforming a carboxylic acid moiety to a borofluoric acid ester by use of an expensive silylating agent (i.e., via silyl ester), making this method cumbersome. Therefore, there is demand for a production method which can be performed in a simpler manner.

Thus, an object of the present invention is to establish a novel process which is friendly to the global environment, the process employing a high-stability, high-handleability cyclic amine salt compound which realizes reaction at high efficiency; avoiding use of an expensive silylating agent; and reducing the process waste.

Means for Solving the Problems

The present inventors have carried out extensive studies on the aforementioned process, and have found that through allowing the compound represented by formula (2), a cyclic amine salt, and a boron derivative to react in a solvent in the presence of a base, quinolonecarboxylic acid derivatives can be efficiently synthesized in a one-pot reaction without forming a silyl ester, thereby realizing an industrially advantageous method for producing a quinolone-based synthetic anti-bacterial agent. The present invention has been accomplished on the basis of this finding.

The present invention is directed to a method for producing a compound represented by formula (1):

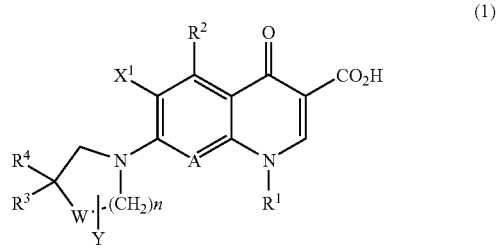

[wherein
$R^1$ represents an optionally substituted C1 to C6 alkyl group, an optionally substituted C3 to C6 cycloalkyl group, an optionally substituted phenyl group, or an optionally substituted heteroaryl group;
$R^2$ represents an optionally substituted amino group, a hydrogen atom, a hydroxyl group, a thiol group, a halogenonethyl group, a C1 to C6 alkyl group, a C2 to C6 alkenyl group, a C2 to C6 alkynyl group, or a C1 to C6 alkoxy group;
each of $R^3$ and $R^4$ independently represents a C3 to C6 cycloalkyl group, a hydrogen atom, a halogen atom, a phenyl group, a C1 to C6 alkyl group, a C1 to C6 alkoxy group, a C2 to C6 alkenyl group, or a C2 to C6 alkynyl group, wherein the cycloalkyl group may have an amino group as a substituent; each of the alkyl group, alkoxy group, alkenyl group, and alkynyl group may be linear or branched; and the alkyl group may have one or more substituents selected from the group consisting of a hydroxyl group, an amino group, a halogen atom, a C1 to C6 alkylthio group, a C1 to C6 alkoxy group, a C3 to C6 cycloalkyl group, a C1 to C6 alkylamino group, a C3 to C6 cycloalkylamino group, a C1 to C6 alkoxy group, a phenyl group which may be substituted by a C1 to C6 alkoxy group or halogen atom, a furyl group which may be substituted by a C1 to C6 alkoxy group or halogen atom, and a thiazolyl group which may be substituted by a C1 to C6 alkoxy group or halogen atom, or $R^3$ and $R^4$ may be linked together to form
(a) a spiro-ring structure of a 3- to 6-membered ring structure including the carbon atom to which $R^3$ and $R^4$ are bonded, wherein the spiro ring may have a nitrogen atom, an oxygen atom, or a sulfur atom, as a ring-member atom; the formed ring may be substituted by a halogen atom, a C1 to C6 alkyl group, or an amino group; and the alkyl group may have a group selected from the group consisting of a halogen atom, a C1 to C6 alkyl group, and a C1 to C6 alkoxy group, as a substituent, or (b) an exo-methylene group bonded via a double bond, wherein the exo-methylene group may have one or two substituents selected from the group consisting of a hydroxyl group, an amino group, a halogen atom, a C1 to C6 alkylthio group, and a C1 to C6 alkoxy group;

"A" represents a nitrogen atom or a partial structure represented by the following formula:

(wherein $X^2$ represents a hydrogen atom, a hydroxyl group, a cyano group, a halogen atom, a C1 to C6 alkyl group, a C1 to C6 alkoxy group, a halogenomethyl group, or a halogenomethoxy group, wherein $X^2$ and the above-mentioned $R^1$ may be integrated with a part of the skeleton, to form a ring, and the formed ring may have a C1 to C6 alkyl group as a substituent);

W represents —$CHR^5$—, —O—, or —$NR^6$— (wherein $R^5$ represents a hydrogen atom, a halogen atom, a C1 to C6 alkyl group, a C3 to C6 cycloalkyl group, a C2 to C6 alkenyl group, a C2 to C6 alkynyl group, or a C1 to C6 alkoxy group; the cycloalkyl group may have an amino group as a substituent; the alkyl group may have one or more substituents selected from the group consisting of a hydroxyl group, an amino group, a halogen atom, a C1 to C6 alkylthio group, and a C1 to C6 alkoxy group; $R^5$ and the above-mentioned $R^3$ or $R^4$ may together form a C3 to C6 cycloalkane or a 5- to 7-membered saturated heterocycle with a carbon atom to which these $R^5$ are bonded; and the formed cycloalkane or saturated heterocycle may have a C1 to C6 alkyl group or an amino group as a substituent, and $R^6$ represents a hydrogen atom, a C1 to C6 alkyl group, or a C3 to C6 cycloalkyl group);

$X^1$ represents a hydrogen atom or a halogen atom;

Y represents a hydrogen atom, or an amino group, a C1 to C6 alkyl, a C1 to C6 alkylamino group, a C3 to C6 cycloalkyl group, or a group which can be readily transformed by chemical means to an amino group or a C1 to C6 alkylamino group, these groups each being bonded to any carbon atom of the saturated heterocyclic ring; and n is 0 to 2], a salt thereof, or a hydrate of the compound or salt, characterized in that the method comprises allowing to cause a reaction in a mixture containing a compound represented by formula (2):

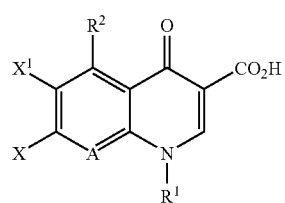

(wherein X represents a halogen atom, and $R^1$, $R^2$, $X^1$, and A have the same meanings as defined above), a salt of a compound represented by formula (3):

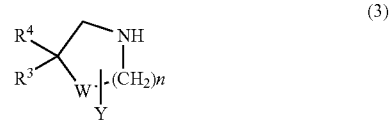

(wherein W, Y, $R^3$, $R^4$, and n have the same meanings as defined above], and a boron derivative in a solvent in the presence of a base, to thereby form a boron chelate compound, and removing a boron chelate moiety from the boron chelate compound.

Effects of the Invention

According to the present invention, a quinolonecarboxylic acid derivative is converted to a borofluoric acid ester or a boric acid ester thereof, which has enhanced reactivity for producing a quinolone derivative, and the formed boron-containing derivative is employed as a starting material of condensation reaction. Therefore, the boron-containing derivative is condensed with a cyclic amine salt compound having high stability and handleability in the presence of a base in one reaction mixture. This process can be performed in a simple manner without isolating the boron-containing derivative, thereby reducing isolation loss. Since the condensation reaction can be performed in a one-pot manner, possible exposure of workers to harmful intermediates can be reduced, and the production yield can be remarkably enhanced. Therefore, from an industrial viewpoint, a target compound represented by formula (1) can be produced at high yield in a simple manner.

Best Modes for Carrying Out the Invention

The quinolonecarboxylic acid compound employed in the present invention is represented by formula (2):

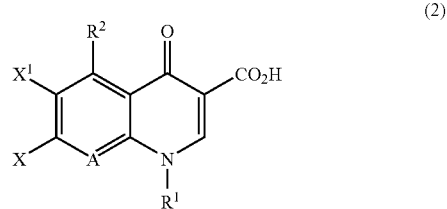

(wherein $R^1$ represents an optionally substituted C1 to C6 alkyl group, an optionally substituted C3 to C6 cycloalkyl group, an optionally substituted phenyl group, or an optionally substituted heteroaryl group;

$R^2$ represents an optionally substituted amino group, a hydrogen atom, a thiol group, a halogenomethyl group, a C1 to C6 alkyl group, a C2 to C6 alkenyl group, a C2 to C6 alkynyl group, or a C1 to C6 alkoxy group;

X represents a halogen atom;

$X^1$ represents a hydrogen atom or a halogen atom; and

"A" represents a nitrogen atom or a partial structure represented by the following formula:

(wherein $X^2$ represents a hydrogen atom, a hydroxyl group, a cyano group, a halogen atom, a C1 to C6 alkyl group, a C1 to CG alkoxy group, a halogenomethyl group, or a halogenomethoxy group, wherein $X^2$ and $R^1$ may be integrated with a part of the skeleton, to form a ring, and the formed ring may have a C1 to C6 alkyl group as a substituent). Hereinafter, the compound is referred to as compound (2).

When $R^1$ is an optionally substituted C1 to C6 alkyl group, examples of the substituent include a halogen atom, a C1 to C6 alkyl group, and a C1 to C6 alkoxy group. Of these, a halogen atom is preferred.

When $R^1$ is a C1 to C6 alkyl group, the alkyl group may be linear or branched. Specific examples include methyl, ethyl, isopropyl, sec-butyl, and tert-butyl. Of these, ethyl and tert-butyl are preferred.

When $R^1$ is a halogen-substituted C1 to C6 alkyl group, the alkyl moiety may be linear or branched. Specific examples include methyl, ethyl, propyl, isopropyl, butyl, isobutyl, sec-butyl, and tert-butyl. Of these, ethyl and tert-butyl are preferred. The halogen atom which serves as a substituent of the alkyl group is preferably a fluorine atom or a chlorine atom, more preferably a fluorine atom. Examples of such halogen-substituted alkyl groups include fluoromethyl, trifluoromethyl, 1-fluoroethyl, 2-fluoroethyl, 2,2,2-trifluoroethyl, 1,1-dimethyl-2-fluoroethyl, 1-methyl-1-(fluoromethyl)-2-fluoroethyl, and 1,1-(difluoromethyl)-2-fluoroethyl. Of these, 2-fluoroethyl and 1,1-dimethyl-2-fluoroethyl are preferred.

When $R^1$ is an optionally substituted C3 to C6 cycloalkyl group, example of the cycloalkyl group include cyclopropyl, cyclobutyl, and cyclopentyl. Of these, cyclopropyl is preferred. The substituent of the cycloalkyl group is preferably a halogen atom, a methyl group, or a phenyl group, more preferably a halogen atom. The halogen atom is preferably a fluorine atom or a chlorine atom, with a fluorine atom being particularly preferred. The number of the substituent on the cycloalkyl group may be 1 or 2, but is preferably 1. In other words, a monofluorocyclopropyl group is preferred, with a 1,2-cis-2-fluorocyclopropyl being more preferred, a (1R,2S)-2-fluorocyclopropyl group being particularly preferred.

When $R^1$ is an optionally substituted phenyl group, examples of the substituent include a halogen atom, a C1 to C6 alkyl group, and a C1 to C6 alkoxy group. Of these, a halogen atom is preferred.

When $R^1$ is a halogen-substituted phenyl group, the halogen atom is preferably a fluorine atom or a chlorine atom, more preferably a fluorine atom. The number of halogen atom substituted on the phenyl group is preferably 1 or 2. The halogen-substituted phenyl group may further have a substituent. The substituent is preferably amino, hydroxyl, or methyl. Examples of such optionally substituted halogen-substituted phenyl groups include a 2-fluorophenyl group, a 4-fluorophenyl group, a 2,4-difluorophenyl group, and a 5-amino-2,4-difluorophenyl group. Of these, a 2,4-difluorophenyl group and a 5-amino-2,4-difluorophenyl group are preferred.

When $R^1$ is an optionally substituted heteroaryl group, the heteroaryl group may be a 5-membered or 6-membered aromatic heterocyclic group having one or more heteroatoms selected from among a nitrogen atom, a sulfur atom, and an oxygen atom. Among such a heteroaryl group, a 5- or 6-membered nitrogen-containing aromatic heterocyclic group having 1 or 2 nitrogen atoms is preferred. Specific examples include pyridyl, pyrimidyl, pyridazinyl, imidazolyl, thiazolyl, and oxazolyl. Of these, pyridyl is preferred.

When $R^1$ is an optionally substituted heteroaryl group, examples of the substituent include a halogen atom, a C1 to C6 alkyl group, and a C1 to C6 alkoxy group. Of these, a halogen atom is preferred. The halogen atom is preferably a fluorine atom or a chlorine atom, more preferably a fluorine atom. The number of halogen atom substituted on the heteroaryl group is 1 or 2. The preferable examples further include an amino group and a hydroxyl group as well as a methyl group.

The halogen-substituted heteroaryl group may further have a substituent. Such an optionally substituted halogen-substituted heteroaryl group is preferably a 6-amino-3,5-difluoropyridin-2-yl group.

The aforementioned $R^1$ is preferably a cyclopropyl group or a 1,2-cis-2-fluorocyclopropyl group, more preferably a (1R,2S)-2-fluorocyclopropyl group.

$R^2$ represents a hydrogen atom, an amino group, a hydroxyl group, a thiol group, a halogenomethyl group, a C1 to C6 alkyl group, a C2 to C6 alkenyl group, a C2 to C6 alkynyl group, or a C1 to C6 alkoxy group.

When $R^2$ is an amino group, the amino group may have one or two groups selected from the group consisting of a formyl group, a C1 to C6 alkyl group, and a C2 to C5 acyl group, as substituents.

When $R^2$ is a C1 to C6 alkyl group, the alkyl group may be linear or branched and is preferably methyl, ethyl, propyl, or isopropyl, with methyl being particularly preferred.

When $R^2$ is a halogenomethyl group, the halogen atom is preferably a fluorine atom, and the number of halogen atoms may be 1 to 3.

When $R^2$ is an amino group, a hydroxyl group, or a thiol group, these groups may be protected by a generally-employed protective group.

Examples of such protective groups include (substituted) alkoxycarbonyl groups such as tert-butoxycarbonyl and 2,2,2-trichloroethoxycarbonyl; (substituted) aralkyloxycarbonyl groups such as benzyloxycarbonyl, p-methoxybenzyloxycarbonyl, and p-nitrobenzyloxycarbonyl; (substituted) acyl groups such as acetyl, methoxyacetyl, trifluoroacetyl, chloroacetyl, pivaloyl, formyl, and benzoyl; (substituted) alkyl groups and (substituted) aralkyl groups such as tert-butyl, benzyl, p-nitrobenzyl, p-methoxybenzyl, and triphenylmethyl; (substituted) ethers such as methoxymethyl, tert-butoxymethyl, tetrahydropyranyl, and 2,2,2-trichloroethoxymethyl; and (alkyl- and/or aralkyl-substituted) silyl groups such as trimethylsilyl, isopropyldimethylsilyl, and tert-butyldiphenylsilyl. Compounds protected with such a substituent are particularly preferred as intermediates for producing quinolone carboxylic acid derivatives.

Examples of the C1 to C6 alkoxy group include methoxy, ethoxy, propoxy, and butoxy. Of these, methoxy is preferred.

The C2 to C6 alkenyl group or the C2 to C6 alkynyl group preferably has two carbon atoms.

Among the aforementioned $R^2$s, a hydrogen atom, an amino group, a hydroxyl group, a methyl group, and a methoxy group are preferred, with a hydrogen atom and an amino group being particularly preferred.

X represents a halogen atom, and $X^1$ represents a hydrogen atom or a halogen atom. Examples of such halogen atoms include a fluorine atom, a chlorine atom, a bromine atom, and an iodine atom. $X^1$ is preferably a hydrogen atom or a fluorine atom.

"A" represents a nitrogen atom or a partial structure represented by formula (II):

($X^2$ represents a hydrogen atom, a hydroxyl group, a cyano group, a halogen atom, a C1 to C6 alkyl group, a C1 to C6 alkoxy group, a halogenomethyl group, or a halogenomethoxy group).

When A is a partial structure represented by formula (II) and $X^2$ is a C1 to C6 alkyl group, the alkyl group may be linear or branched, and is preferably methyl, ethyl, propyl, or isopropyl. Of these, methyl and ethyl are more preferred, with methyl being still more preferred. The C1 to C6 alkoxy group may be an alkoxy group derived from the aforementioned alkyl group. Among such groups, a C1 to C3 alkyl group and a C1 to C3 alkoxy group are preferred, with methyl and methoxy being particularly preferred.

The halogen atom is preferably a fluorine atom or a chlorine atom, more preferably a fluorine atom. The halogen atom of the halogenomethyl group is preferably a fluorine atom or a chlorine atom, more preferably a fluorine atom. Examples of the halogenomethyl group include fluoromethyl, difluoromethyl, and trifluoromethyl. Similarly, the halogen atom of the halogenomethoxy group is preferably a fluorine atom or a chlorine atom, more preferably a fluorine atom. Examples of the halogenomethoxy group include fluoromethoxy, difluoromethoxy, and trifluoromethoxy.

When A is a partial structure represented by formula (II), $X^2$ and $R^1$ may form a cyclic structure together with a part of the quinolone skeleton (3-atom-structure; i.e., the carbon atom to, which $X^2$ is bonded, the nitrogen atom to which $R^1$ is bonded, and the carbon atom to which both of the former carbon atom and the latter nitrogen atom are bonded). The thus-formed ring is preferably a 5- to 7-membered ring and may be saturated or unsaturated. The cyclic structure may have an oxygen atom, a nitrogen atom, or a sulfur atom, as a ring-member atom and may be further substituted by a C1 to C6 alkyl group as mentioned in relation to $X^2$. Preferably, the cyclic structure has an oxygen atom and is preferably substituted by a methyl group. An example of preferred such structures is —O—CH$_2$—CH(—CH$_3$)—, in which the carbon atom at the right end is bonded to a nitrogen atom.

When A is a partial structure represented by formula (II) and the substituent $X^2$ does not form a cyclic structure, $X^2$ is preferably methyl, ethyl, methoxy, difluoromethoxy, cyano, a fluorine atom, or a chlorine atom, particularly preferably methyl, methoxy, or difluoromethoxy.

When A is a partial structure represented by formula (II) and the substituent $X^2$ forms a cyclic structure, the cyclic structure is preferably a 2,3-dihydro-3-methyl-7-oxo-7H-pyrido[1,2,3-de][1,4]benzoxazine-6-carboxylic acid skeleton. Among such skeletons, 3-(S)-methylpyridobenzoxazine skeleton is particularly preferred.

According to the method of the present invention, a cyclic amino substituent having a second amine moiety is introduced to the 7-position or an equivalent site of the quinolon compound from compound (3). Examples of such substituents include (7S)-7-amino-7-methylspiro[2.4]hept-5-yl, 3-methylaminopiperidin-1-yl, 4-methylpiperazin-1-yl, and the following substituents.

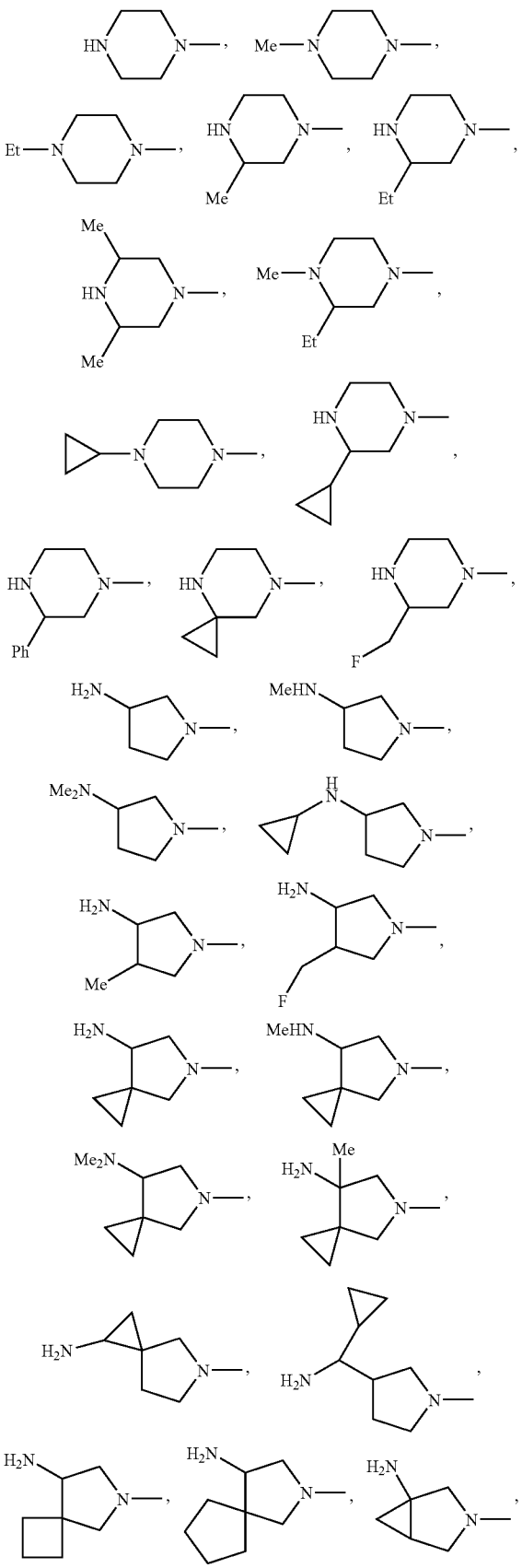

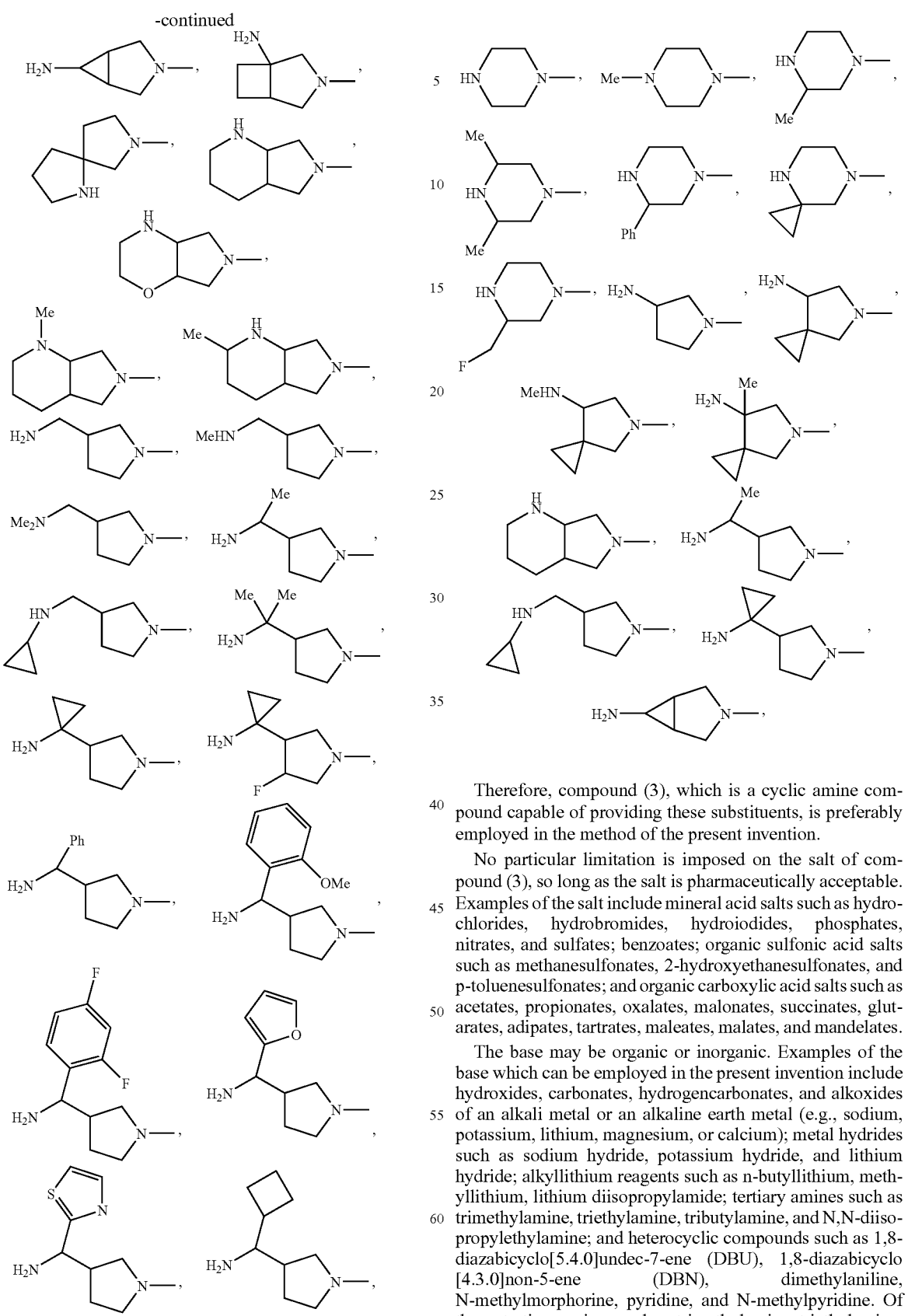

Among them, preferred are the following groups.

Therefore, compound (3), which is a cyclic amine compound capable of providing these substituents, is preferably employed in the method of the present invention.

No particular limitation is imposed on the salt of compound (3), so long as the salt is pharmaceutically acceptable. Examples of the salt include mineral acid salts such as hydrochlorides, hydrobromides, hydroiodides, phosphates, nitrates, and sulfates; benzoates; organic sulfonic acid salts such as methanesulfonates, 2-hydroxyethanesulfonates, and p-toluenesulfonates; and organic carboxylic acid salts such as acetates, propionates, oxalates, malonates, succinates, glutarates, adipates, tartrates, maleates, malates, and mandelates.

The base may be organic or inorganic. Examples of the base which can be employed in the present invention include hydroxides, carbonates, hydrogencarbonates, and alkoxides of an alkali metal or an alkaline earth metal (e.g., sodium, potassium, lithium, magnesium, or calcium); metal hydrides such as sodium hydride, potassium hydride, and lithium hydride; alkyllithium reagents such as n-butyllithium, methyllithium, lithium diisopropylamide; tertiary amines such as trimethylamine, triethylamine, tributylamine, and N,N-diisopropylethylamine; and heterocyclic compounds such as 1,8-diazabicyclo[5.4.0]undec-7-ene (DBU), 1,8-diazabicyclo[4.3.0]non-5-ene (DBN), dimethylaniline, N-methylmorphorine, pyridine, and N-methylpyridine. Of these, tertiary amines such as trimethylamine, triethylamine, tributylamine, and N,N-diisopropylethylamine, and heterocyclic compounds such as 1,8-diazabicyclo[5.4.0]undec-7- ene (DEU), 1,8-diazabicyclo[4.3.0]non-5-ene (DBN), dimethylaniline, N-methylmorphorine, pyridine, and N-methylpyridine are preferred, with triethylamine being particularly preferred. The base is generally used in an amount, with respect to the amount of compound (2), 3 to 10 times by mole (mole ratio), particularly preferably used in an amount of 4 to 6 times by mole (mole ratio).

No particular limitation is imposed on the solvent used in the present invention, so long as it does not impede the reaction. Examples of hydrocarbon solvents include n-hexane, n-pentane, benzene, toluene, xylene, chlorobenzene, and xylene. Examples of alcohol solvents include methanol, ethanol, propanol, isopropanol (IPA), n-butanol, and t-butanol. Examples of ether solvents include diethyl ether, diisopropyl ether (IPE), methyl t-butyl ether (MTBE), tetrahydrofuran (THF), cyclopentyl methyl ether, dimethoxyethane, and 1,4-dioxane. Examples of amide solvents include dimethylformamide (DMF), dimethylacetamide (DMAc), and N-methyl-2-pyrrolidone (NMP). Examples of cyclic urea solvents include 1,3-dimethyl-2-imidazolidinone (DMI), and 1,3-dimethyl-3,4,5,6-tetrahydro-2(1H)-pyrimidinone (DMPU). Examples of halohydrocarbon solvents include chloroform, methylene chloride, and 1,2-dichloroethane (EDC). Examples of the solvent further include dimethyl sulfoxide (DMSO), sulforan, acetonitrile, acetate esters, and acetone. These solvents may be used singly or in combination of two or more species. Among these solvents, amide solvents include dimethylformamide (DMF), dimethylacetamide (DMAc), and N-methyl-2-pyrrolidone (NMP), and acetonitrile are preferred, with acetonitrile being particularly preferred. The amount of solvent, which cannot be predetermined unequivocally, is generally about 1 to about 100 times by weight with respect to that of compound (2), preferably about 5 to about 15 times by weight.

The boron derivative is preferably a trihalogenoboron compound, more preferably a trifluoroboron compound. Trifluoroboron is preferably used in the form of an ether complex. Examples of such ether complexes include diethyl ether complex and tetrahydrofuran complex. The boron derivative is generally used in an amount, with respect to the amount of compound (2), 1 to 10 times by mole (mole ratio), particularly preferably used in an amount of 1.5 to 3 times by mole (mole ratio).

In the method of the present invention, a tertiary amine salt is preferably present in the reaction mixture. Among such salts, tertiary amine acid-adduct salts are preferably used. No particular limitation is imposed on the tertiary amine, so long as the amine is tertiary nature, and any of aliphatic amines, aromatic amines, saturated or unsaturated heterocyclic amines, and complex amines thereof may be employed. Examples of the tertiary amine include the aforementioned trialkylamines (e.g., triethylamine, N,N-diethylisopropylamine, and tributylamine); dialkylarylamines (e.g., dimethylaniline and diethylaniline); N-methylmorphorine; and N-methylpiperidine. The acid which forms the acid-adduct salt may be an inorganic acid or an organic acid. Examples of the acid include inorganic acids such as hydrochloric acid and sulfuric acid; organic carboxylic acids such as formic acid, acetic acid, propionic acid, butyric acid, oxalic acid, and malonic acid; and sulfonic acids such as p-toluenesulfonic acid, benzenesulfonic acid, methanesulfonic acid, naphthalenesulfonic acid, trifluoromethanesulfonic acid, and camphorsulfonic acid. Among these salts, inorganic salts are preferred, and, for example, hydrochlorides are preferably employed. Generally, the amount of the tertiary amine salt employed with respect to that of compound (2) is preferably about 1 to 10 times by mole (mole ratio), particularly preferably 1.5 to 3 times by mole (mole ratio).

The tertiary amine salt is preferably added, particularly when the acid which forms the cyclic amine salt compound for introducing a substituent is an weak acid.

The reaction temperature may fall within a range of room temperature to the boiling point of the solvent. The reaction completes within a period of about 30 minutes to 78 hours.

Through the aforementioned procedure, a quinolone carboxylic acid compound in which the carboxylic acid moiety has been transformed to a boron chelate substituent is produced. The boron chelate substituent is removed through hydrolysis after completion of reaction with a cyclic amine. When the amino group has been protected, the amino group is deprotected, whereby a quinolone compound of interest can be produced. No particular limitation is imposed on the conditions under which hydrolysis to remove a boron substituent is performed, and the hydrolysis is performed under generally employed conditions. For example, the hydrolysis may be performed in a hydrated alcoholic solvent containing methanol, ethanol, etc., or in a hydrated amide solvent containing dimethylformamide (DMF), dimethylacetamide (DMAc), N-methyl-2-pyrrolidone (NMP), etc. with heating. The reaction is preferably performed at a temperature between 80° C. and the boiling point of the employed solvent. Deprotection may be performed under suitable conditions depending on the employed protective group. For example, the aforementioned hydrolyzate is subjected to hydrogenolysis or treatment with concentrated hydrochloric acid. After completion of reaction, the reaction mixture is alkalinized with, for example, aqueous sodium hydroxide, and neutralized with an appropriate acid such as hydrochloric acid. The precipitated crystals are recovered through filtration, or extracted with a solvent such as chloroform. The thus-produced compound is purified through, for example, dissolution in an appropriate solvent for recrystallization, whereby a quinolone compound of interest can be yielded.

EXAMPLES

The present invention will next be described in detail by way of examples, which should not be construed as limiting the invention thereto.

Example 1

7-[(7S)-7-Amino-7-methylspiro[2.4]hept-5-yl]-1,4-dihydro-6-fluoro-1-[(1R,2S)-2-fluorocyclopropyl]-8-methoxy-4-oxo-3-quinolinecarboxylic acid dihydrate An acetonitrile solution (800 mL) containing 6,7-difluoro-1,4-dihydro-1-[(1R,2S)-2-fluorocyclopropyl]-8-methoxy-4-oxo-3-quinolinecarboxylic acid (90 g), benzyl-(7S)-7-methyl-5-azaspiro[2.4]heptan-7-amine dihydrochloride (90 g), triethylamine (39.9 mL), and boron trifluoride-tetrahydrofuran complex (63.4 mL) was stirred at room temperature for 30 minutes. Boron trifluoride-tetrahydrofuran complex (6.3 mL) was further added to the solution, followed by stirring for one hour at the same temperature. Triethylamine (159.5 mL) was further added to the reaction mixture, followed by stirring at room temperature for 16 hours. The solvent was evaporated under reduced pressure, and methanol (900 mL) was added to the residue. The mixture was refluxed for 6 hours. After cooling to room temperature, the mixture was stirred at 40° C. for 5 hours under hydrogen in the presence of 5% Pd—C (4.5 g). Subsequently, triethylamine (90 mL) and water (225 mL) were added to the thus-obtained reaction mixture, followed by stirring at 40° C. for one hour. Pd—C was removed through filtration, and the filtrate was concentrated under reduced pressure. Water (720 mL) and methanol (180 mL) were added to the residue, and the pH of the product was adjusted to 8 by use of 5N aqueous sodium hydroxide solution. The thus-obtained mixture was stirred at 60° C. for 40 minutes, and the pH of the product was adjusted to 7 by use of 5N aqueous sodium hydroxide solution, followed by stirring at room temperature for one hour. The thus-produced crystals were recovered through filtration and dried, to thereby yield 120.9 g of the title compound as pale brown crystals (yield: 91%).

$^1$H-NMR (400 MHz, 0.1N-NaOD) δppm: 0.48-0.56 (2H, m), 0.66-0.76 (2H, m), 1.12 (3H, s), 1.42-1.63 (2H, m), 3.55 (3H, s), 3.59-3.72 (4H, m), 3.98-4.03 (1H, m), 4.79-5.03 (1H, m), 7.65 (1H, d, J=13.9 Hz), 8.44 (1H, s)

Elemental analysis: Calc. C, 55.38%; H, 5.93%; N, 9.07% Obsd. C; 55.19%; H; 5.98%, N; 9.19%

Example 2

7-[(7S)-7-Amino-7-methylspiro[2.4]hept-5-yl]-1,4-dihydro-6-fluoro-1-[(1R,2S)-2-fluorocyclopropyl]-8-methoxy-4-oxo-3-quinolinecarboxylic acid dihydrate An acetonitrile solution (24 mL) containing 6,7-difluoro-1,4-dihydro-1-[(1R,2S)-2-fluorocyclopropyl]-8-methoxy-4-oxo-3-quinolinecarboxylic acid (3 g), (7S)-7-methyl-5-azaspiro[2.4]heptan-7-amine dihydrochloride (3 g), triethylamine (1.34 mL), and boron trifluoride-tetrahydrofuran complex (2.68 g) was stirred at room temperature for 30 minutes. Boron trifluoride-tetrahydrofuran complex (0.27 g) was further added to the solution, followed by stirring for one hour at the same temperature. Triethylamine (5.37 mL) was further added to the reaction mixture, followed by stirring at room temperature for 5 hours. The solvent was evaporated under reduced pressure, and methanol (30 mL) was added to the residue. The mixture was refluxed for 2 hours, and the solvent was evaporated. 90% Hydrated methanol was added to the residue, and the pH of the product was adjusted to 8 by use of 5N aqueous sodium hydroxide. The thus-obtained mixture was stirred at 60° C. for 40 minutes, and the pH of the product was adjusted to 7 by use of 5N aqueous sodium hydroxide solution, followed by stirring at 5° C. for 16 hours. The thus-produced crystals were recovered through filtration and dried, to thereby yield 4.23 g of the title compound (yield: 93%). Spectral data of this compound coincided with those obtained in Example 1.

Example 3

1-Cyclopropyl-1,4-dihydro-6-fluoro-8-methoxy-7-(3-methylaminopiperidin-1-yl)-4-oxo-3-quinolinecarboxylic acid dihydrate An acetonitrile solution (30 mL) containing 1-cyclopropyl-6,7-difluoro-1,4-dihydro-8-methoxy-4-oxo-3-quinolinecarboxylic acid (3 g), 3-methylaminopiperidine dihydrochloride (2.1 g), triethylamine (1.43 mL), and boron trifluoride-tetrahydrofuran complex (2.84 g) was stirred at room temperature for 2 hours. Triethylamine (5.71 mL) was further added to the reaction mixture, followed by stirring at room temperature for 24 hours. The solvent was evaporated under reduced pressure, and methanol (30 mL) was added to the residue. The mixture was refluxed for 6 hours, and the solvent was evaporated under reduced pressure. 80% Hydrated methanol (30 mL) was added to the residue, and the pH of the product was adjusted to 8 by use of 5N aqueous sodium hydroxide solution, followed by stirring at room temperature for 16 hours. The thus-produced crystals were recovered through filtration and dried, to thereby yield 3.98 g of the title compound (yield: 92%).

$^1$H-NMR (400 MHz, DMSO-d$_6$) δppm: 0.90-1.31 (4H, m), 1.31-2.12 (4H, m), 2.67-3.71 (5H, m), 3.77 (3H, s), 3.98-4.09 (1H, m), 7.85 (1H, d, J=11.1 Hz), 8.78 (1H, s)

Elemental analysis: Calc. C; 56.69%, H; 6.62%; N; 9.74% Obsd. C; 56.48%, H, 6.63%, N; 9.86%

Example 4

1-Cyclopropyl-1,4-dihydro-6-fluoro-8-methoxy-7-(3-methyl-1-piperazinyl)-4-oxo-3-quinolinecarboxylic acid ½ hydrate An acetonitrile solution (30 mL) containing 1-cyclopropyl-6,7-difluoro-1,4-dihydro-8-methoxy-4-oxo-3-quinolinecarboxylic acid (3 g), 2-methylpiperazine dihydrochloride (1.93 g), triethylamine (1.43 mL), and boron trifluoride-tetrahydrofuran complex (2.84 g) was stirred at room temperature for one hour. Triethylamine (5.71 mL) was further added to the reaction mixture, followed by stirring at room temperature for 24 hours. The solvent was evaporated under reduced pressure, and methanol (30 mL) was added to the residue. The mixture was refluxed for 5 hours, and the solvent was evaporated under reduced pressure. 80% Hydrated methanol (30 mL) was added to the residue, and the pH of the product was adjusted to 7 by use of 5N aqueous sodium hydroxide solution, followed by stirring at room temperature for 16 hours. The thus-produced crystals were recovered through filtration and dried, to thereby yield 3.55 g of the title compound (yield: 91%).

$^1$H-NMR (400 MHz, CDCl$_3$) δppm: 1.02-1.31 (7H, m), 2.92-3.53 (7H, m), 3.77 (3H, s), 3.91-4.11 (1H, m), 7.85 (1H, d, J=12.3 Hz), 8.79 (1H, s)

Elemental analysis: Calc. C; 59.37%, H; 6.03%, N; 10.93% Obsd. C; 59.49%, H; 5.77%, N; 11.03%

Example 5

9-Fluoro-(3S)-methyl-10-(4-methylpiperazin-1-yl)-7-oxo-2,3-dihydro-7H-pyrido[1,2,3-de]-1,4-benzoxazine-6-carboxylic acid An acetonitrile solution (30 mL) containing 9,10-difluoro-(3S)-methyl-7-oxo-2,3-dihydro-7H-pyrido[1,2,3-de]-1,4-benzoxazine-6-carboxylic acids (3 g), 4-methylpiperazine dihydrochloride (2.22 g), triethylamine (1.43 mL), and boron trifluoride-tetrahydrofuran complex (2.84 g) was stirred at room temperature for 30 minutes.

Triethylamine (5.71 mL) was further added to the reaction mixture, followed by stirring at room temperature for 24 hours. The solvent was evaporated under reduced pressure, and methanol (30 mL) was added to the residue. The mixture was refluxed for 24 hours, and the solvent was evaporated under reduced pressure. Ethanol (15 mL) was added to the residue, and the mixture was stirred at room temperature for 16 hours. The thus-produced crystals were recovered through filtration and dried, to thereby yield 3.55 g of the title compound (yield: 92%).

$^1$H-NMR (400 MHz, CDCl$_3$) δppm: 1.63 (3H, d, J=7 Hz), 2.38 (3H, s), 2.54-2.60 (4H, m), 3.40-3.44 (4H, m), 4.35-4.52 (3H, m), 7.76 (1H, d, J=11.8 Hz), 8.64 (1H, s)

Elemental analysis: Calc. C; 59.82%, H; 5.58%, N; 11.63% Obsd. C; 60.01%, H; 5.69%, N; 11.53%

Example 6

7-[(3R)-3-(1-tert-Butoxycarbonylaminocyclopropyl)-pyrrolidin-1-yl]-1-[(1R,2S)-2-fluorocyclopropyl]-1,4-dihydro-8-methoxy-4-oxo-3-quinolinecarboxylic acid An acetonitrile solution (45 mL) containing 7-fluoro-1-[(1R,2S)-2-fluorocyclopropyl]-8-methoxy-4-oxo-1,4-dihydro-3-quinolinecarboxylic acid (3 g), triethylamine hydrochloride (2.8 g), and boron trifluoride-tetrahydrofuran complex (2.84 g) was stirred at room temperature for 30 minutes. tert-Butyl {1-[(3R)-pyrrolidin-3-yl]cyclopropyl}carbamate oxalic acid salt (3.54 g) and triethylamine (5.71 mL) were further added to reaction mixture, followed by stirring for 10 hours at the same temperature. The solvent was evaporated under reduced pressure, and methanol (30 mL) was added to the residue. The mixture was refluxed for 12 hours, and the solvent was evaporated under reduced pressure. 80% Hydrated methanol (20 mL) was added to the residue, and the pH of the product was adjusted to 7 by use of 5N aqueous sodium hydroxide solution, followed by stirring at 60° C. for 30 minutes and at room temperature for 16 hours. The thus-produced crystals were recovered through filtration and dried, to thereby yield 4.79 g of the title compound (yield: 94%).

$^1$H-NMR (400 MHz, CDCl$_3$) δppm: 0.68-0.95 (4H, m), 1.29-1.58 (2H, m), 1.42 (3H, s), 1.71-1.91 (1H, m), 2.03-2.15 (1H, m), 2.22-2.40 (1H, m), 3.36-3.71 (4H, m), 3.52 (3H, s), 3.79-3.90 (1H, m), 4.74-5.05 (1H, m), 4.99 (1H, brs), 6.94 (1H, d, J=9.2 Hz), 8.06 (1H, d, J=9.2 Hz), 8.65 (1H, d, J=3.1 Hz), 15.18 (1H, brs)

Elemental analysis: Calc. C; 62.26%, H; 6.43%, N, 8.38% Obsd. C; 62.14%, H; 6.47%, N; 8.43%

The invention claimed is:

1. A method for producing a compound represented by formula (1):

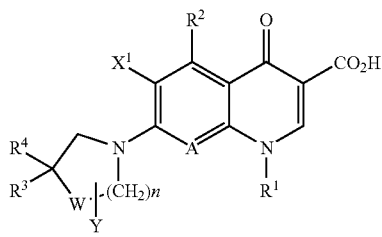

wherein
R$^1$ represents
a C1 to C6 alkyl group,
a C3 to C6 cycloalkyl group,
a phenyl group,
a heteroaryl group,
a C1 to C6 alkyl group substituted with a halogen atom, a C1 to C6 alkyl group, or a C1 to C6 alkoxy group,
a C3 to C6 cycloalkyl substituted with a halogen atom, a methyl group, or a phenyl group,
a phenyl group substituted with a halogen atom, a C1 to C6 alkyl group, or a C1 to C6 alkoxy group,
a heteroaryl group substituted with a halogen atom, a C1 to C6 alkyl group, and a C1 to C6 alkoxy group;
R$^2$ represents an amino group, a hydrogen atom, a hydroxyl group, a thiol group, a halogenomethyl group, a C1 to C6 alkyl group, a C2 to C6 alkenyl group, a C2 to C6 alkynyl group, a C1 to C6 alkoxy group, or an amino group substituted with one or two substituents selected from the group consisting of a formyl group, a C1 to C6 alkyl group, and a C2 to C5 acyl group;

each of R$^3$ and R$^4$ independently represents a C3 to C6 cycloalkyl group, a hydrogen atom, a halogen atom, a phenyl group, a C1 to C6 alkyl group, a C1 to C6 alkoxy group, a C2 to C6 alkenyl group, or a C2 to C6 alkynyl group, wherein the cycloalkyl group may have an amino group as a substituent; each of the alkyl group, alkoxy group, alkenyl group, and alkynyl group may be linear or branched; and the alkyl group may have one or more substituents selected from the group consisting of a hydroxyl group, an amino group, a halogen atom, a C1 to C6 alkylthio group, a C1 to C6 alkoxy group, a C3 to C6 cycloalkyl group, a C1 to C6 alkylamino group, a C3 to C6 cycloalkylamino group, a phenyl group which may be substituted by a C1 to C6 alkoxy group or a halogen atom, a furyl group which may be substituted by a C1 to C6 alkoxy group or a halogen atom, and a thiazolyl group which may be substituted by a C1 to C6 alkoxy group or a halogen atom, or R$^3$ and R$^4$ may be linked together to form (a) a spiro-ring structure of a 3- to 6-membered ring structure including the carbon atom to which R$^3$ and R$^4$ are bonded, wherein the Spiro ring may have a nitrogen atom, an oxygen atom, or a sulfur atom, as a ring-member atom; the formed ring may be substituted by a halogen atom, a C1 to C6 alkyl group, or an amino group; and the alkyl group may have a group selected from the group consisting of a halogen atom, a C1 to C6 alkyl group, and a C1 to C6 alkoxy group, as a substituent, or (b) an exo-methylene group bonded via a double bond, wherein the exo-methylene group may have one or two substituents selected from the group consisting of a hydroxyl group, an amino group, a halogen atom, a C1 to C6 alkylthio group, and a C1 to C6 alkoxy group;

"A" represents a nitrogen atom or a partial structure represented by the following formula:

wherein X$^2$ represents a hydrogen atom, a hydroxyl group, a cyano group, a halogen atom, a C1 to C6 alkyl group, a C1 to C6 alkoxy group, a halogenomethyl group, or a halogenomethoxy group, wherein X$^2$ and R$^1$ may form a 5- to 7-membered ring including the carbon atom to which X$^2$ is bonded, the nitrogen atom to which R$^1$ is bonded, and the carbon atom to which both of the former carbon atom and the latter nitrogen atom are bonded, and the formed ring may have a C1 to C6 alkyl group as a substituent;

W represents —CHR$^5$—, —O—, or —NR$^6$— wherein R$^5$ represents a hydrogen atom, a halogen atom, a C1 to C6 alkyl group, a C3 to C6 cycloalkyl group, a C2 to C6 alkenyl group, a C2 to C6 alkynyl group, or a C1 to C6 alkoxy group; the cycloalkyl group may have an amino group as a substituent; the alkyl group may have one or more substituents selected from the group consisting of a hydroxyl group, an amino group, a halogen atom, a C1 to C6 alkylthio group, and a C1 to C6 alkoxy group; R$^5$ and R$^3$ or R$^4$ may together form a C3 to C6 cycloalkane or a 5- to 7-membered saturated heterocycle with a carbon atom to which these Rs are bonded; and the formed cycloalkane or saturated heterocycle may have a C1 to C6 alkyl group or an amino group as a substituent, and $R^6$ represents a hydrogen atom, a C1 to C6 alkyl group, or a C3 to C6 cycloalkyl group;

$X^1$ represents a hydrogen atom or a halogen atom;

Y represents a hydrogen atom, or an amino group, a C1 to C6 alkyl, a C1 to C6 alkylamino group, a C3 to C6 cycloalkyl group, or a group which can be readily transformed by chemical means to an amino group or a C1 to C6 alkylamino group, these groups each being bonded to any carbon atom of the saturated heterocyclic ring; and n is 0 to 2, a salt thereof, or a hydrate of the compound or salt, wherein the method comprises reacting a mixture comprising a compound represented by formula (2):

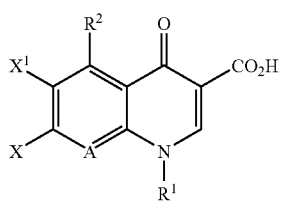

wherein X represents a halogen atom, and $R^1$, $R^2$, $X^1$, and A have the same meanings as defined for formula (1), a salt of a compound represented by formula (3):

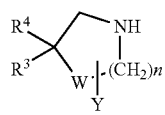

wherein W, Y, $R^3$, $R^4$, and n have the same meanings as defined for formula (1) and a trifluoroboron compound in a solvent in the presence of a base, to form a boron chelate compound, and removing a boron chelate moiety from the boron chelate compound.

2. The method according to claim 1, wherein the trifluoroboron compound is a trifluoroboron-diethyl ether complex or a trifluoroboron-tetrahydrofuran complex.

3. The method according to claim 1, wherein the base is a salt of a tertiary amine.

4. The method according to claim 1, wherein the solvent is a hydrocarbon solvent, an alcohol solvent, an ether solvent, diethyl ether, an amide solvent, a cyclic urea solvent, a halohydrocarbon solvent, dimethyl sulfoxide (DMSO), sulforan, acetonitrile, acetate ester, acetone, or a combination thereof.

5. The method according to claim 1, wherein the solvent is dimethylformamide (DMF), dimethylacetamide (DMAc), N-methyl-2-pyrrolidone (NMP), or acetonitrile.

6. The method according to claim 1, wherein the base is a hydroxide, a carbonate, a hydrogencarbonate, or an alkoxide of an alkali metal or an alkaline earth metal, a metal hydride, an alkyllithium reagent, a tertiary amine, a heterocyclic compound, or a combination thereof.

7. The method according to claim 4, wherein the base is a tertiary amine or a heterocyclic compound.

8. The method according to claim 1, wherein the base is trimethylamine, triethylamine, tributylamine, N,N-diisopropylethylamine, 1,8-diazabicyclo[5.4.0]undec-7-ene (DBU), 1,8-diazabicyclo[4.3.0]non-5-ene (DBN), dimethylaniline, N-methylmorphorine, pyridine, or N-methylpyridine.

9. The method according to claim 1, wherein the base is triethylamine.

10. The method according to claim 1, wherein the trifluoroboron compound is present in a mole ratio relative to compound (2) of from 1 to 10.

11. The method according to claim 1, wherein the trifluoroboron compound is present in a mole ratio relative to compound (2) of from 1.5 to 3.

12. The method according to claim 3, wherein the salt of a tertiary amine is a tertiary amine acid-adduct salt.

13. The method according to claim 3, wherein the salt of a tertiary amine is trialkylamine salt, a dialkylarylamine salt, a N-methylmorphorine salt, or a N-methylpiperidine salt.

14. The method according to claim 3, wherein the salt of the tertiary amine is a hydrochloride.

* * * * *